(12) United States Patent
Kostiainen et al.

(10) Patent No.: US 7,863,559 B2
(45) Date of Patent: Jan. 4, 2011

(54) METHOD AND APPARATUS FOR MASS SPECTROMETRIC ANALYSIS

(75) Inventors: Risto Kostiainen, Helsinki (FI); Samuli Franssila, Helsinki (FI); Tapio Kotiaho, Espoo (FI); Seppo Marttila, Nurmijärvi (FI)

(73) Assignee: Licentia Oy, Helsinki (FI)

( * ) Notice: Subject to any disclaimer, the term of this patent is extended or adjusted under 35 U.S.C. 154(b) by 585 days.

(21) Appl. No.: 10/579,225

(22) PCT Filed: Nov. 15, 2004
(Under 37 CFR 1.47)

(86) PCT No.: PCT/FI2004/000683

§ 371 (c)(1),
(2), (4) Date: Mar. 24, 2008

(87) PCT Pub. No.: WO2005/047848

PCT Pub. Date: May 26, 2005

(65) Prior Publication Data

US 2009/0108193 A1     Apr. 30, 2009

(30) Foreign Application Priority Data

Nov. 14, 2003   (FI) .................................. 20031658

(51) Int. Cl.
   *H01J 49/10*   (2006.01)
(52) U.S. Cl. ........................ 250/288; 250/281; 250/282
(58) Field of Classification Search ................. 250/281, 250/282, 288, 283; 96/15, 16, 17, 20, 101, 96/105; 95/82, 83, 84, 85, 87; 73/19.02, 73/23.22, 23.55
See application file for complete search history.

(56) References Cited

U.S. PATENT DOCUMENTS

| | | |
|---|---|---|
| 5,170,052 A | 12/1992 | Kato |
| 5,259,254 A | 11/1993 | Zhu et al. |
| 5,750,988 A | 5/1998 | Apffel et al. |

(Continued)

FOREIGN PATENT DOCUMENTS

| | | |
|---|---|---|
| EP | 0452930 A2 | 10/1991 |
| JP | 60127453 A | 7/1985 |
| JP | 2000088808 A | 3/2000 |
| WO | 0015321 A1 | 3/2000 |
| WO | 00/41214 A1 | 7/2000 |

OTHER PUBLICATIONS

Daniel D. Ebeling, Michael S. Westphall, Mark Scalf, and Lloyd M. Smith, "Corona Discharge in Charge Reduction Electrospray Mass Spectrometry", Analytical Chemistry, vol. 72, No. 21, Nov. 1, 2000, pp. 2-5.

(Continued)

*Primary Examiner*—Jack I Berman
*Assistant Examiner*—Nicole Ippolito Rausch
(74) *Attorney, Agent, or Firm*—Sughrue Mion, PLLC

(57) ABSTRACT

A method and an apparatus for examining a sample by means of mass spectrometry. According to the method, the solution comprising the sample to be examined is vaporized in a vaporizer, the vaporized sample solution is sprayed, using a gas flow, into a corona discharge zone, where the examined sample is ionised according to the APCI method, using a corona discharge, to generate gas phase ions, and the ions are separated and directed to a detector. According to the present invention, a vaporizer is used, which is fabricated as a micro-mechanical structure which comprises the flow channels for the solution and for the carrier gas possibly used for feeding the solution, as well as the heater of the vaporizer, and which are all included in a monolithic structure. The solution is especially suitable for cases in which a very sensitive analysing technique is needed, or in which the available sample quantity is very small (less than 1 µL).

30 Claims, 5 Drawing Sheets

U.S. PATENT DOCUMENTS

| | | | |
|---|---|---|---|
| 6,563,111 | B1 | 5/2003 | Moon et al. |
| 6,569,324 | B1 | 5/2003 | Moon et al. |
| 6,579,452 | B1 | 6/2003 | Moon et al. |
| 6,610,978 | B2 | 8/2003 | Yin et al. |
| 6,649,908 | B2 * | 11/2003 | Apffel et al. ............ 250/288 |
| 7,208,729 | B2 * | 4/2007 | Syms ...................... 250/288 |
| 7,435,952 | B2 * | 10/2008 | Finlay et al. ............ 250/292 |
| 2002/0123153 | A1 | 9/2002 | Moon et al. |
| 2002/0158027 | A1 | 10/2002 | Moon et al. |
| 2003/0146377 | A1 * | 8/2003 | Miller et al. ............ 250/286 |
| 2005/0199805 | A1 * | 9/2005 | Freidhoff ................ 250/294 |
| 2006/0071161 | A1 * | 4/2006 | Syms ...................... 250/290 |
| 2006/0151694 | A1 * | 7/2006 | Guevremont et al. .... 250/292 |

OTHER PUBLICATIONS

Office Action issued Jul. 6, 2010 by Japanese Patent Office in counterpart Japanese Application No. 2006-538878.

* cited by examiner

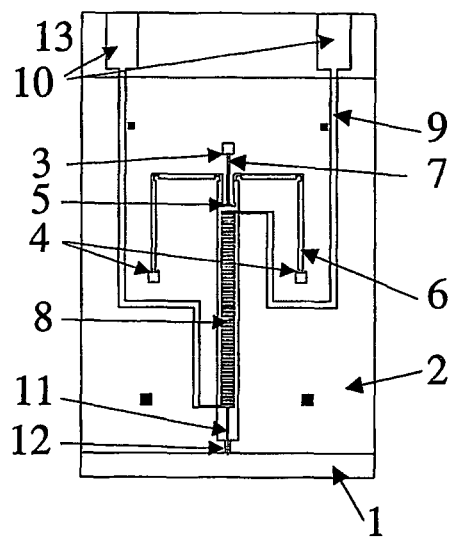
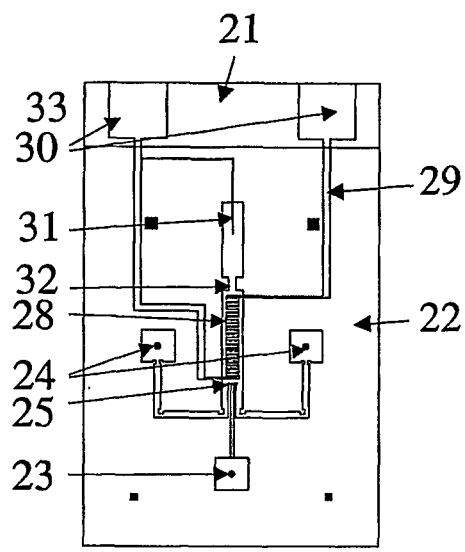
Fig. 3a
Fig. 3c
Fig. 3b
Fig. 3d

METHOD AND APPARATUS FOR MASS SPECTROMETRIC ANALYSIS

This Application is a 371 of PCT/FI2004/000683, filed Nov. 15, 2004; the disclosure of which is incorporated herein by reference.

The present invention relates to a method according to the preamble of claim 1 of examining a sample by means of mass spectrometry.

According to such a method, a solution containing the sample to be examined is first vaporised and, using a gas stream, the vaporised sample solution is then sprayed into the immediate vicinity of a corona discharge needle, where the sample to be examined is ionised. The charged particles are separated and, using electric and/or magnetic fields, conducted to a detector.

The present invention also relates to an apparatus according to the preamble of claim 17, and to a use according to claim 30.

Mass spectrometry is used in many fields of science, such as pharmaceutical research, genetics, environmental analyses and particle research. In mass spectrometry (hereinafter also abbreviated as "MS") material is examined on the basis of data about its mass, and with MS it is possible, among other things, to identify the compounds of a chemical sample and to determine their quantity ($<10^{-11}$ M) in very small percentages, from complex sample matrices.

Typically, the sample to be examined is ionised in the ioniser of the mass spectrometer into a gaseous form and the gas-phase ions thus generated are separated on the basis of their mass/charge ratio (m/z) using electric and/or magnetic fields (mass analyser). The gas-phase ions are observed using a detector. The spectrum of the mass is established from a graph of the strength of the ionic current, which is generated by the detector, as a function of the m/z value of the ion.

The most commonly used method of ionising liquid samples is electrospray ionisation (ESI), where the sample, which is dissolved in a polar solvent, for example methanol, is introduced into a mass spectrometer through a thin needle-shaped capillary tube. When the capillary is exposed to high voltage (3-5 kV), a strong electrostatic field is formed at the tip of the capillary and, as a result, a charged aerosol is formed in the gaseous phase from the solution coming out of the capillary. The charged droplets of the aerosol emit gaseous-phase ions into the gaseous phase, and using a separate atmospheric pressure ion source they are collected in the mass analyser. In the ESI the ionisation takes place at normal pressure and it is suitable for examining even large molecules (MW>100 kDa).

In the Atmospheric Pressure Chemical Ionization (APCI) method, the eluent is passed through a thin steel capillary which is installed inside a bigger steel tube. Between the tubes a spray gas is passed, causing the eluent to nebulize. The aerosol mist is led through a heated quartz tube, where the solvent and the compounds to be examined are vaporised. The vapour generated is ionised by means of a corona discharge electrode, to which a high voltage (3-5 kV) is connected. As a result of the electric discharge, the compound to be examined is ionised in the gaseous phase. The generated ions are collected for a mass analysis using an API dispatch. Unlike electric nebulizing, this method is suitable also for neutral molecules. In APCI, both polar and non-polar solvents can be used as the eluent, whereas in the ESI only polar solvents can be used.

The accompanying FIG. 1 shows in more detail the principle of APCI ionisation. In the immediate vicinity of the tip of the electrode (needle), which is connected to a high potential, the strength of the electric field exceeds the corona discharge threshold of air, and the molecules (for instance $N_2$, $O_2$) in the air are ionised and changed into primary ions ($N_2^+$, $O_2^+$). The primary ions react with the solvent molecules (for instance $H_2O$, $CH_3OH$, $NH_3$) forming reagent ions (for instance $H_3O^+$, $CH_3OH_2^+$, $NH_4^+$). The reagent ions react with the sample molecules forming protonized ($[M+H^+]$) or deprotonized ($[M-H]^-$) molecules, which can be analyzed by mass spectrometry.

Depending on the type of the sample, the APCI ionisation is carried out either in a positive or negative mode. In the positive mode, the potential of the needle is higher than that of the curtain plate and the ionisation usually takes place by a proton transfer reaction. The proton transfer takes place according to Formula I (see below) if the proton affinity is higher than the proton affinity of the reagent gas:

$$XH^+ + M \rightarrow X + MH^+ \qquad (I)$$

In the negative mode, the potential of the needle is higher than that of the curtain plate and the ionisation takes place by deprotonation (II, see below) or electron transfer (III, see below). In the deprotonation, the reagent molecule has a higher proton affinity than the sample molecule. The electrons generated in the plasma in the electron transfer react with the sample molecules, which have a high electron affinity.

$$(X-H)^- + M \rightarrow X + (M-H)^- \qquad (II)$$

$$M + e^- \rightarrow M^- \qquad (III)$$

The most commonly used solvents are aqueous solutions of methanol ($CH_3OH$) or methylcyanide ($CH_3CN$). Protonation or deprotonation can be intensified by adding small amounts of additives to the solvent. For instance, ammonium acetate ($CH_3COONH_4$) can be used in positive mode, and acetic acid ($CH_3COOH$) and formic acid (HCOOH) in negative mode.

Because the compounds to be examined are brought into the gaseous phase by heating, the compound is fragmented more than in the ESI method. However, because the heating is very rapid, the compound is often not fragmented completely and a protonized or a deprotonized molecule is observed in the spectrum. The heating effect is separately optimized depending on the solvent/sample used. Usually, the temperature of the inner surface of the capillary is 100-150° C. The generation of an effective spraying demands a rapid flow of the spray gas, approximately 2 l/min. In the APCI ionisation, the charge number of ions is usually one, which makes it possible to determine the molecular weight of the compound. On the basis of the fragments generated, information about the structure of the molecule can be achieved.

Feeding the analyte to the APCI ionisator takes place using a spray pump or a HPLC (High Performance Liquid Chromatography) pump. Using the pump, the flow can be adjusted even for very small quantities of liquid. In a conventional APCI, the flow of liquid is usually approximately 0.2-1 ml/min. By contrast, a gas flow is clearly higher than that, generally approximately 2 l/min. APCI is most suitable for ionisation of molecules of, at most, a few thousand Da.

A precondition for the corona to discharge is that the strength of the electric field exceeds the corona threshold value. In order to avoid an electrical breakdown, the electric field must be clearly non-homogeneous. A non-homogeneous electric field can be generated for instance by means of a sharp, needle-shaped electrode. In this case, the peak value of the electric field is located around the tip of the needle.

APCI is more suitable than ESI for analysing neutral compounds. In APCI, both polar and non-polar solvents can be used, whereas only polar solvents can be used in ESI. Moreover, high percentages of buffer agents or additives interfere with the ionisation clearly more in the ESI method than in the APCI. A disadvantage of APCI is that the sample speeds and flow speeds needed are significantly high. APCI is suitable only for flow speeds over 100 µl/min, and consequently, conventional APCI devices cannot be used for instance in microfluidic systems. Beyond that, the sensitivity of traditional APCI devices is not sufficient for small sample quantities.

Other disadvantages of known devices are relatively high manufacturing and operating costs, too. The latter costs include for instance substantial time spent for cleaning the devices.

The purpose of the present invention is to eliminate the disadvantages associated with the known technology and to generate a completely new way of examining samples in gas or liquid phase using mass spectrometry. In particular, the purpose of the present invention is to generate a working solution which is based on an APCI ion source, better suited to analysing small sample quantities than the devices used today. Another purpose of the present invention is to improve the sensitivity of APCI devices, and the heat transfer inside the vaporiser, too. Beyond that, a purpose of the present invention is to lower the manufacturing and the operating costs of the APCI devices.

The present invention is based on the idea that an APCI ioniser, suitable for analysing small sample quantities, is fabricated using micro mechanics. Miniaturized ESI solutions are already known, where flow channels for the sample solution and an injection tip used for ionising are machined in a monolithic, small glass plate. (Hereinafter, these devices are also called "ESI micro chips" or "µ-ESI devices"). Known technologies are described in U.S. Pat. Nos. 6,481,648 and 6,245,227. As with ESI technology in general, these miniaturized devices are suitable for ion-like compounds, but not for neutral and non-polar compounds, which cannot be ionised with ESI or for which the efficiency of ionisation is too weak.

The ESI liquid-feeding system is also described in the Published International Applications WO 00/41214, WO 01/53794 and WO 00/62039, and U.S. Pat. No. 5,917,184. In these publications there are no suggestions that the described feeding equipments would be used for vaporising the sample, in which case the equipment would be suitable for APCI. In the application WO 01/53794 there is a reference to heating, but in the known equipment heating is used for pumping of the sample solution. The solution is based on thermal expansion of the sample or bubble formation, and the sample is not vaporised.

An unsolved disadvantage of using known ESI micro chips as miniaturized devices is that the high voltage electric field remains concentrated at the tip of the µ-ESI device, i.e. the exit port of the microfluidic system, which destroys this tip rapidly, which in turn limits the operating life of the µ-ESI and prevents generation of proper and stable analyses. In addition, the oxidation and the reduction reactions taking place at the tip of the ESI sprayer lead to clogging of the tip and formation of bubbles.

Associated with the present invention it has been found that a miniaturization of the process is considerably more appropriate for the APCI technique ioniser than for the ESI ioniser mentioned above. According to the present invention, parts of the device which are typical to the APCI ioniser, at least the flow channel networks for gases and liquid, and the heater of the vaporiser, are included in a monolithic structure, where the flow channels are dimensioned so that the liquid flow is less than approximately 100 µl/min.

In the µ-APCI method, because the high voltage electric field is concentrated at the tip of the corona discharge needle and not at the exit point of the microfluidic system, this exit point is not vulnerable to destruction. Furthermore, at the same time, it is possible to carry out a proper and stable analysis.

By using a device according to the present invention even small sample quantities can be vaporised and they can be ionised in a corona discharge zone, for instance a corona discharge needle, which forms part of the microchip or which is arranged in linkage with the microchip.

More specifically, the method according to the present invention is mainly characterized by what is stated in the characterization part of claim 1.

The device according to the present invention is, in turn, characterized by what is stated in the characterizing part of claim 17.

The use according to the present invention is specified in claim 30.

Considerable advantages can be achieved with the solution according to the present invention. Thus, the manufacturing process of the device is simple enough to yield the required result.

The present invention generates a new interface between any microanalytic system of a microfluidistic type, or any other type, and a mass spectrometer. The device can be used in particular for small flow volumes (less than 5 µl/min), but it is also suitable for flow volumes of as small as approximately 100 µL. The most important fields of application of the present invention are bioanalyses, pharmacological analyses, drug analyses, environmental toxins analyses, food analyses, clinical analyses and diagnostics. The method and the device are especially suitable for cases in which very sensitive analysis techniques are needed, or in which the quantity of the sample available is very small (less than 1 µL).

The present invention can be applied to analysing many kinds of compounds. It is suitable for both polar and non-polar compounds, and for neutral compounds and ionic compounds, too. In principle, it is possible to analyse all compounds which comprise a functional point, such as a functional group that can be protonized. Examples of especially interesting applications are slightly polar compounds, classified as non-polar, in which the percentages of these in the samples are very low. Examples of these are different steroids, such as neurosteroids, which comprise at least one hydroxy group or, correspondingly, ketone group. The quantities of such compounds in biological samples are in the range of 10-100 picograms per millilitre. In addition, the present invention can also be used for analysing alkaline nitrogen compounds, which generally form the main part of, for instance, all pharmacologically active agents.

Consequently, the solution can be used for analysing both liquid and gas phase samples. The eluent used for dissolving the sample can be either a polar and/or a non-polar solvent.

The micro-APCI technique according to the present invention is especially usable for compounds which can be vaporised, especially at normal atmospheric pressure, and the molar masses of which are usually approximately 50-2500 Da, preferably at most 2000 Da, most suitably at most 1000 Da.

Compared to the µ-ESI technique, the P-APCI generates a better sensitivity for analyses of polar and neutral compounds. Non-polar eluents can be used in the analyses, and, if desired, even gas phase samples can be analysed.

Compared to the conventional APCI technique, considerable advantages, too, are achieved with the present invention. Accordingly, in the present invention, the flow rates range from nanolitres to a few dozen microlitres, whereas the conventional APCI is suitable only for flow rates which are higher than 100 μl/min. The present invention can be used for analyzing smaller sample volumes and the device has a significantly better sensitivity than the conventional APCI. In addition, the heat transfer and the vaporisation have been improved.

The costs of production of the μ-APCI are significantly lower than of the conventional APCI. Consequently, the present invention makes it possible, in principle, to manufacture disposable vaporisation/ionisation devices, in which case a spent device, after becoming dirty, can be replaced with a totally new device. This significantly cuts down the time needed for cleaning the MS device.

In the following, the invention will be examined and explained in more detail, with the help of the accompanying drawings.

Figure 1:
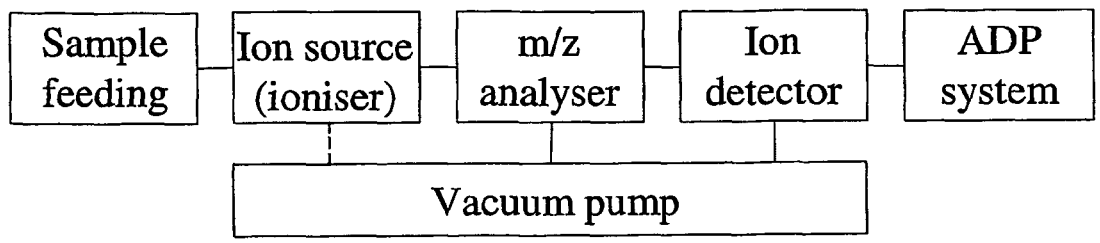
FIG. 1 shows a block diagram of the parts of a mass spectrometer device.
Figure 2:
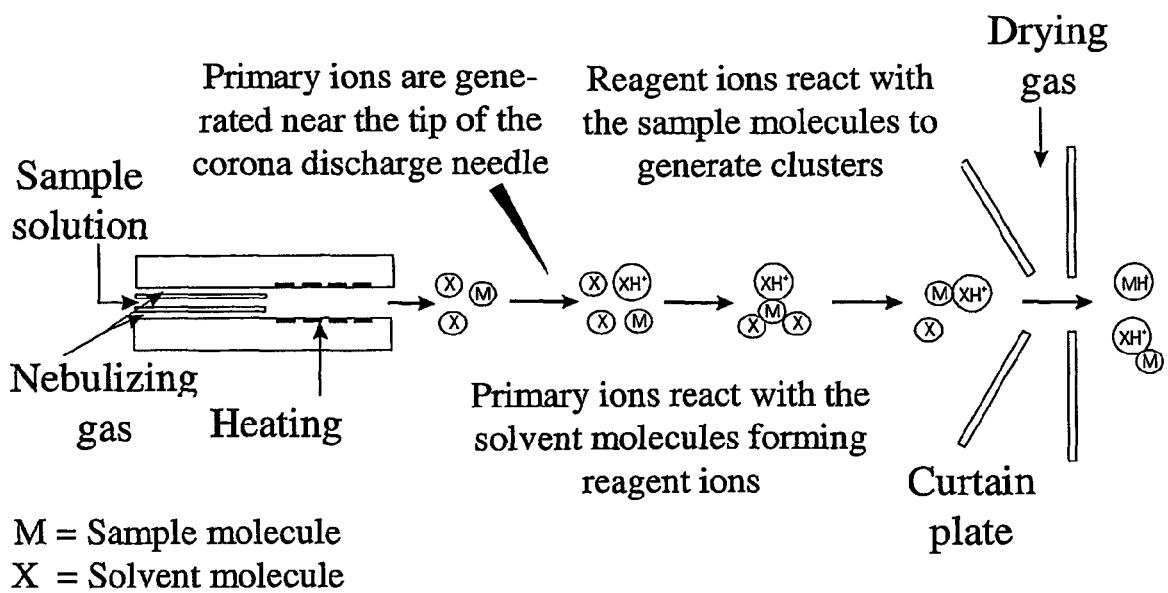
FIG. 2 shows the principle of the basic solution of APCI ionisation.
Figure 4A:
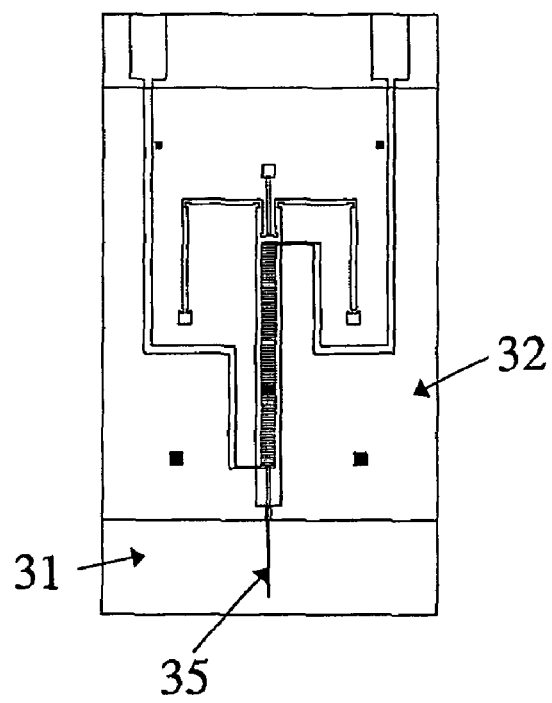
Figure 4B:
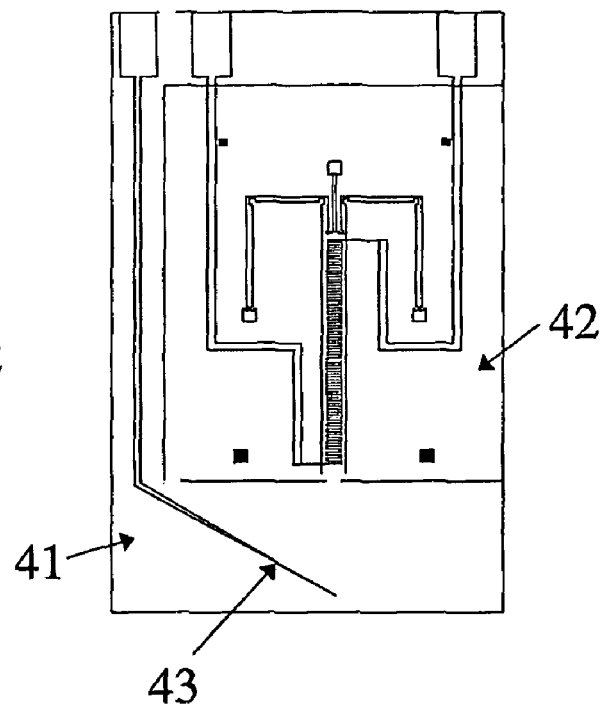
Figure 5A:
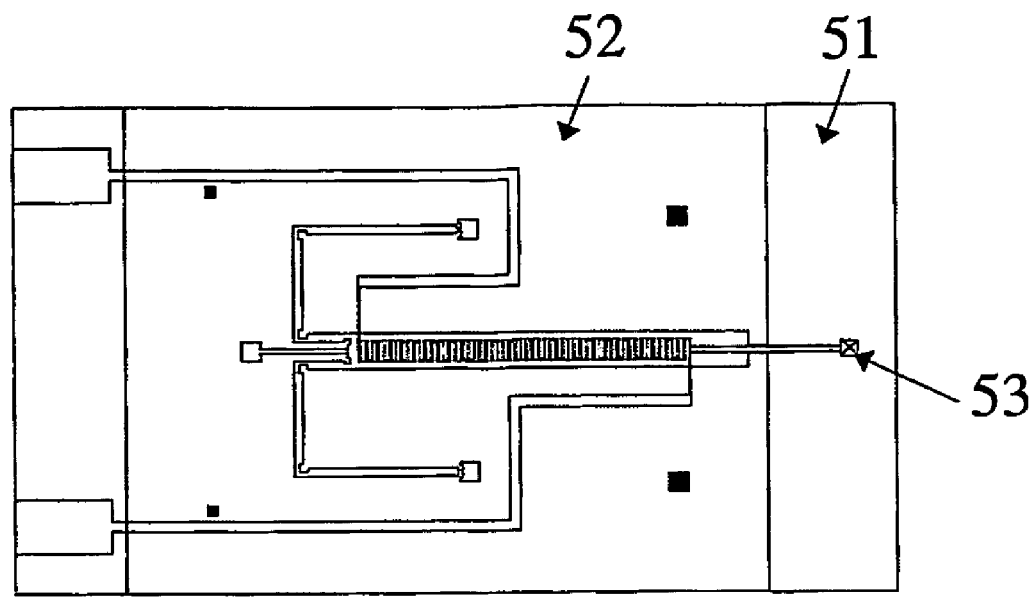
Figure 5B:
Figures 6A, 6B:
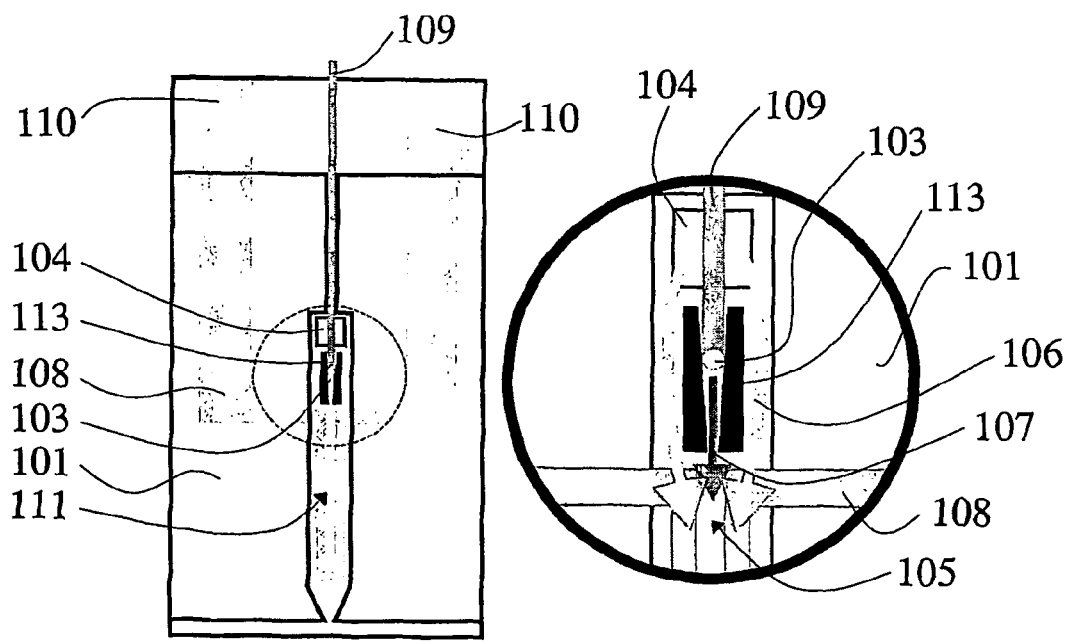
Figure 7:
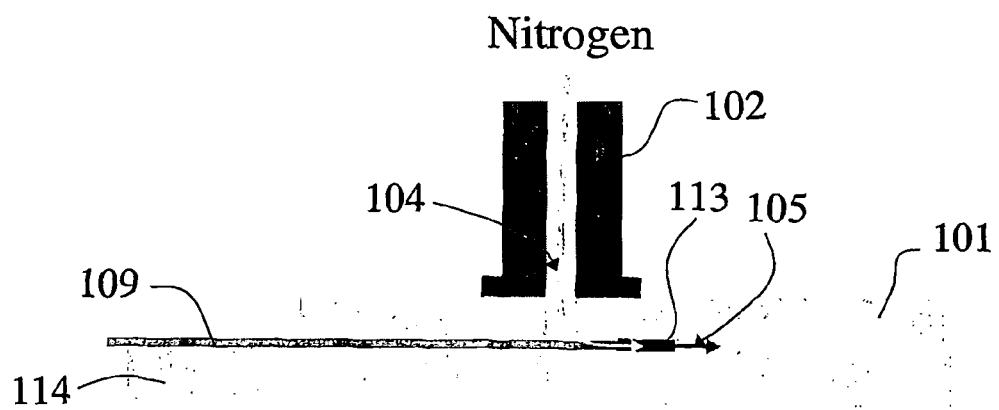

FIG. 3 shows the structures of two alternative embodiments of the device according to the present invention, simplified and depicted from above and from the side, respectively, whereby FIGS. 3a and 3b show the structure of the horizontal micro-APCI ion source and, correspondingly, FIGS. 3c and 3d the structure of the vertical ion source, FIGS. 4a and 4b show the chip configurations of the structures shown in FIG. 3a, as versions modified with a planar needle, FIGS. 5a and 5b show a microchip equipped with a three-dimensional needle, simplified and depicted from above and from the side, respectively, FIGS. 6a and 6b show an alternative feeding system depicted from above, and details of the system, and FIG. 7 shows the application according to FIGS. 6a and 6b depicted from the side.

In known technology, a micro-electromechanical system (MEMS/MST) generally refers to a system where micromechanical and microelectronic structures have been integrated on the same microchip (typical size range 1 $mm^2$-10 $cm^2$). It is known that micromechanical structures (range of dimensions 0.1 μm-1 mm) can be manufactured by etching a substrate wafer (bulk-micromechanics) or by patterning thin films built up on a substrate wafer surface (surface micromechanics). Substrate materials generally used in micromechanics are silicon, glass, GaAs, quartz and plastics. For instance, silicon dioxide, silicon nitride, amorphous/polycrystalline silicon, metals and polymers are used as thin films (thickness range 1 nm-1 mm).

In the present invention, a micronized structure is called simply "a micromechanical structure". By this is meant a unit (size approximately 1 $mm^2$-10 $cm^2$) which is fabricated on a substrate wafer/wafers and which comprises structures, such as channels and resistors, which are essential to the operation of the component.

In the method according to the present invention a solution comprising the sample to be examined is vaporised in a vaporiser in the form of a micromechanical device. The vaporiser comprises a monolithic block in which at least flow channels for the sample solution have been formed, as well as flow channels for a possible carrier gas, plus a heater for the sample solution. The vaporised sample solution generated is sprayed, using a gas flow, into a corona discharge zone, where the sample to be examined is ionised using a corona discharge to produce gas phase ions, after which the ions are separated and led to a detector, using a method, for instance with electrical and/or magnetic fields, which is known per se.

In this invention, a "monolithic" block means a block which comprises only one single part or has been formed of two or more parts, which, using a bonding-technique, have been joined together to form one single block so firmly that the parts can no longer be detached from each other without substantially breaking the parts.

According to a preferred embodiment of the present invention a micromechanical structure is used, one which comprises a substrate wafer or a stack of several connected discs, in which flow channel networks for gases and liquid as well as a heater for vaporising the sample solution have been constructed. In this case, the monolithic block is formed of two or more blocks which have been joined to each other. A single block such as this can comprise smaller blocks all of which are identical or, alternatively, different, and made of, for instance, glass or silicon. Consequently, the flow channels for gases and liquid together with their inlet openings and heater for the vaporiser can be constructed in the same part or in different parts which are placed against each other. The block can, for instance, comprise a glass plate in which the flow channel systems for gases and liquid have been formed, as well as a silicon wafer in which a heater used for vaporising the sample solution is constructed. The structure can be reversed, too.

The entire device can also be made of one material, for example glass. A preferable embodiment of the present invention comprises a device which can be made using either wet or plasma processing (DRIE, deep reactive ion etching), or the channel systems can be made by using sand blasting, too. The masking material can be for instance polycrystalline silicon, amorphous silicon, chromium, nickel or SU-8 epoxy resist, which are built up by sputtering, vaporising, electrochemical deposition or spin-coating. The through holes can be carried out by sand blasting or drilling, too.

SU-8 masking is described in more detail for instance at the address http://www.microchem.com/products/su_eight.htm According to the present invention, the flow channel networks have been dimensioned so that the flow of liquid through them is less than 100 μl/min, most suitably at most approximately 50 μl/min, especially at most approximately 10 μl/min. Generally, the sizes of the channels vary depending on whether the substance flowing through them is gas or liquid. A typical size of a gas-feeding channel (the width or the depth of the cross-section) is approximately 10-1000 μm, especially approximately 20-500 μm, and the corresponding size of the liquid flow channel is approximately 5-500 μm, especially approximately 10-250 μm, though these are not limiting dimensions. The depth of the channels is usually smaller than the height, in which case the depth is usually less than 200 μm. If the cross-section of the channels is circular, their diameter is typically within the general range mentioned above.

The nebulizing gas can be fed either in the direction of the sample or essentially perpendicular to the flow direction of the sample, as is described in more detail below with reference to FIGS. 6a, 6b and 7. The gas flow used in the injection is brought essentially perpendicular to the flow direction of the sample. In both applications the gas flow is fed into the device preferably in the direction of the liquid before the inlet opening of the liquid. When the gas flow is fed in perpendicular direction, through one inlet opening, the gas flow is efficiently distributed around the liquid flow comprising the sample, and the gas is extremely homogeneously mixed with the solution.

According to one embodiment, the vaporiser according the present invention comprises both a vaporising and a corona discharge zone which have been integrated to create one single micromechanical structure. However, it is possible to fabricate the corona discharge zone as a separate part of the device.

The sample solution vaporised in the device is ionised by a corona discharge in the presence of air, according to the APCI method. Most suitably, this is carried out at normal atmospheric pressure. In the vaporisation the sample is heated so much that the material to be examined is sufficiently well vaporising while the compound is still essentially in an undegraded form. Generally the sample is heated to its boiling point, which, depending on the material to be examined, varies between approximately 30 and 350° C. The normal vaporisation temperature is approximately 200-300° C., and at least 20 mole-%, especially at least 40 mole-%, preferably 50-100 mole-% of the sample to be examined is vaporised. Of the vaporised compound/material 5-100 mole-%, preferably at least approximately 10 mole-%, especially at least 20 mole-% (and even 95 mole-%) is in the gaseous phase in an undegraded form.

Typically, the corona discharge zone comprises a needle-shaped electrode, which is connected to a potential which is so high in relation to the curtain plate of the mass spectrometer that the electric field strength, at least in the immediate vicinity of the tip of the electrode, exceeds the corona discharge threshold of air. The potential of the needle-shaped electrode in relation to the curtain plate is, for instance, at least 1 kV and the maximum electric field near the tip of the electrode is approximately 50 kV/mm.

FIGS. 3a-3d, attached, show two embodiments of the present invention. As the figures show, the device according to the present invention can, for example, be fabricated following two different configurations, namely horizontal (FIGS. 3a and 3b) or vertical (FIGS. 3c and 3d). In the horizontal solution, the chip (and, accordingly, the needle and the flow exit port) is perpendicular to the curtain plate of the mass spectrometer, and in the vertical solution the chip is parallel to it.

FIGS. 3a and 3b show the structure of a horizontal μ-APCI ion source. As the lateral view shows, the device comprises a glass plate (1), on which a silicon wafer (2) has been arranged. Into the silicon wafer (2), feeding holes for liquid (3) and, correspondingly, for gas (4) have been machined. The silicon wafer has been equipped with a mixing zone (5), too, to which the feeding holes (3 and 4) for liquid and gas, respectively, have been connected through the feeding tube systems (6 and 7). The mixing zone comprises, for instance, a capillary tube, which has been arranged in the silicon wafer and which has been equipped with a heating resistance (8). In order to vaporise the liquid, this heating resistance can be used to heat the liquid and gas flows which are fed into the capillary and mixed in it. Connected to the heating resistance (8), are electric wires (9), which at one end, i.e. at the glass plate surface, are equipped with contact electrodes (10), to which an electric source can be connected.

In the devices in FIGS. 3a and 3b an electrode needle (11) which produces the corona discharge, has been arranged parallel to the glass plate (1) and the capillary tube (5). The electrode needle (11) is connected through electric wires to the contact electrodes (13), too. At the exit end of the capillary tube there is an orifice (12) from which the ionised gas spray, coming from the electrode needle (11) can be discharged and led to a mass spectrometer to be analysed.

The devices according to FIGS. 3c and 3d are basically of the same structure as the devices described in FIGS. 3a and 3b. Accordingly, there is a glass plate (21), and a silicon wafer (22) on top of it. In this case, however, the feeding holes (23 and 24), for liquid and gas, respectively have been arranged in the glass plate. In the silicon wafer, a mixing zone (25) has been machined to which gas and, correspondingly, liquid can be led through their respective feeding tube systems (26 and 27). The device is equipped with a heater (28), including its electric wires (29) and contact electrodes (30), which surround the mixing zone (capillary no. 25). The electrode needle (31) is arranged horizontally towards the mixing zone orifice (32).

The ionisers shown in FIGS. 3a-3d can be fabricated for instance by etching the channel networks (5-7; 25) into the silicon disc, using anisotropic wet etching. The metallic planar needle (11, 31) and the heater (8, 28) are patterned in the glass plate, which is finally attached to the silicon wafer using anodic bonding.

The advantages of this solution are easiness of etching and bonding.

Besides anodic bonding, the joining can be carried out for instance by glass frit bonding, thermo-compression bonding or glue bonding, in which case conventional polymer-based adhesives can be used as intermediate agents. Typical examples are epoxy-polymers, negative and positive resists, polyimides, PMMA, silicones and fluoro-elastomers.

Generally, the polymer glue seam is not hermetic and it does not withstand high temperatures, but on the other hand the bonding can be carried out at low temperatures (depending on the polymer, even at below 100° C.) and for a large variety of materials, which makes it an attractive alternative in, for instance, CMOS processes. The glue bonding method comprises careful washing and drying of the discs/chips to be connected, spreading of adhesion promoter, spinning/spraying of polymer (thickness for instance 1-20 μm) on both or one of the surfaces to be connected, prebake-heat treatment (for instance 60-100° C., 10 min), placing the discs/chips under compression in a vacuum chamber, and the hardbake-heat treatment (for instance at 100-300° C., 5 min).

The present invention can also be constructed entirely of glass, which is a solution that further improves the thermal and electrical properties of the device.

Depending on the testing device, the width of the gas feeding channels of the fabricated testing devices has been 270, 320 or 370 μm. The liquid feeding channel, in turn, has been 120, 130 or 140 μm, and the width of the mixing/heating channel 1.27 mm. The length of the feeding hole side has been 670 μm in the horizontal model and in the vertical model almost 2 mm, because of the glass drilling allowance. The depth of the channels has varied between 85 μm and 190 μm, because of the anisotropy of the etching (narrowness of the channels).

The planar heater and needle can be patterned in the metal layer which is sputtered, vaporised or built up in some other way on the glass plate (1 and 21, respectively). The metal can be a precious metal, such as platinum, or a base metal which has a high electrical and/or thermal conductivity, such as aluminium, and which is inert enough for the sample to be examined. The thickness of the metal layer to be built up can be freely chosen; in the testing solution a thickness of 300 nm was chosen, in which case the resistance at room temperature was approximately 85-90Ω for the horizontal chips, and for the vertical chips approximately 43Ω.

The length of the electrode needle is usually approximately 0.5-10 mm, preferably approximately 1-6 mm. The testing devices were fabricated using a needle length of 2 or 3 mm for the horizontal model, and 2 or 2.5 mm for the vertical model.

At the points of the contact electrodes, the silicon can be made thinner by etching, and thereby make the electrodes emerge from the silicon-glass interface. It is not advantageous to etch through the silicon at these points because the physical strength of the wafer (with regard to the bonding) may suffer. A three-dimensional microneedle eliminates this problem, because, in this case, there would be ample volumes of ionisable gas in the immediate vicinity of the tip of the needle. Due to the miniaturization of the ion source, analysing small quantities of samples (flow magnitude µl/min) is easier and the measuring sensitivity improves.

In the following, a practical example of the process of manufacturing the present ionisers is described:

A 380 µm thick n-type (100) wafer, polished on both sides, was chosen as the silicon substrate of the chip. High-resistance (>500 Ωcm) wafers were used to fabricate the prototypes, in order to reduce the leakage of current from the heater. A 0.5 mm thick glass wafer of type Corning Pyrex 7740, which can be anodically bonded to the silicon, was used as the chip cap.

The manufacturing process started with RCA-washing of the silicon wafers. Organic contamination was removed by means of RCA-1-washing and metallic contamination by RCA-2-washing. A HF-dip was carried out between the washings. After the washings, a thermal oxide of approximately 600 nm was built up on the silicon wafers, using a wet oxidisation process. A HMDS layer was vaporised onto the oxidised wafers to improve the adhesion of the resist, after which a 1.4 µm photoresist (AZ 5214) was spun onto the wafers. After the prebake, the resist was exposed through mask no. 1. After the development of the layer and the hardbake, the oxide was removed by etching from the channel areas. After the oxide etching, the resist was removed with acetone and isopropanol.

When the channel areas had been patterned on the front side of the silicon wafer, the lead-ins were patterned on the reverse side of the wafer. The resisting of this reverse side was carried out in the same way as described above. The Electronic Visions AL-6 device with microscopes above and under the wafer was used as a locator for two-sided registering. After the registering and the exposure, the development, hardbake, possible resisting of the front side, oxide etching and resist removal were carried out once again.

The etching of the wafers was carried out in a 20 m-% TMAH solution at 80° C. Because of the water-circulated heating and the vapour barrier of the etching vessel, the temperature of the entire etching solution was kept constant throughout the process. Moreover, the wearing of the etcher by vaporising was minimal. The etching time was 9 hours. When the etching was completed, the wafers were rinsed very thoroughly in bubbling DI water to ensure that the TMAH residues would leave no film on the surface of the wafers.

Pyrex glass wafers, the processing of which started with acetone and isopropanol washing, were chosen as the initial material for the glass plates. After careful drying, an aluminium layer of approximately 300 µm was sputtered onto the glass wafer in an Oxford sputter. Following the sputtering, a photoresist, which was applied onto the aluminium layer, was patterned with the mask no. 3, using photolithography. Excess aluminium was removed in an aluminium etcher containing phosphoric acid. After that, the inlet holes of the vertical model chip were drilled in the glass. For the drilling, the glass wafer was resisted on both sides and glued, using resist, to the silicon wafer so that the bonded side was uppermost. A 0.8 mm diamond-coated hard metal tip and DI-water cooling were used for the drilling. After the drilling, the wafers were separated from each other using acetone washing in an ultrasonic basin.

The last stage of operation was to attach the processed silicon and glass wafers to each other using anodic bonding. A bonder type comprising a bonding chamber, a control unit and a mechanical vacuum pump was used for the bonding. The bonding chamber comprised heaters above and under the wafer, plus altogether four probes for measuring the temperature, a pressure probe and a press operated by compressed air. The control unit can be used to regulate the temperature of the chamber, the pressure, the compression and the voltage/current across the package of wafers.

After bonding, the sawing of the chips was carried out. It was possible to reveal the contact pads at the interface after the sawing by bending away the thin silicon strip on top of them. Finally, the fluidic connectors were glued to the chips using epoxy glue.

The inlet connectors which enable connecting of the micro hoses were glued to the chips. Using commercial inlet connectors, it was possible to attach the capillaries to the chips by screwing them on, resulting in a tight and easily releasable connection. The outside diameter of the liquid and the gas capillary was 360 µm and the inside diameter 150 µm.

It was decided that the operation of the micro channel networks would be studied using a video camera attached to a microscope. A nitrogen flow was connected to the heated chip, and, using an injection pump, the test sample was fed into the micro channel network. The test sample used was fluoresin, which was dissolved in methanol and, using a xenon lamp, tuned to be gleaming. During the measuring, the flow rate of the liquid was maintained at a few µl/min. This method can be employed to observe how the micro channel network operated under regimes of different gas and liquid flow rates. It was found that the frequency at which the micro droplets—which formed at the end of the liquid channel— detached largely depended on the flow rate of the gas. During the measuring, the feeding pressure of the gas used was several bars at most, but it was difficult to estimate the actual flow rate. If the heating was switched on, the droplets were rapidly vaporised from the end of the liquid channel.

To connect the horizontal and the vertical model chips to the mass spectrometer, supports made of Teflon were fabricated for both them.

For the test measurements, the chip was connected to a API 300 series mass spectrometer, manufactured by PE Sciex Instruments.

The mass spectrometer's own 8 kV source was used as the high voltage source. Batteries (12 V or 24 V) were used as the power source for the heater. A multimeter was used to measure the current through the heater. A separate flow pump, which could be used to regulate the flow at a µl/min-level, was used for the pumping of the sample solution. Depending on the gas used, either the mass spectrometer's own feeding system or a separate gas feeding system was used to feed the nebulizing gas.

Midazolam ($C_{18}H_{13}ClFN_3$, M=325.8) and pyridin ($C_5H_5N$, M=79.1), dissolved in methanol, were used as test solutions. Midazolan is a drug that has a very high proton affinity. Pyridin, too, has a high proton affinity and also a low boiling point (115° C.).

The measurements were carried out in a so called "heated nebulizer" mode, and it was decided that they would begin using the mass spectrometer's own corona discharge needle. To begin with, air was used as the nebulizing gas because it was possible to regulate its flow with the controlling programme of the mass spectrometer. The testing of the horizontal model was started using only solvent (methanol). The basic parameters used are shown below:

Flow rate of sample: 1 µl/min
Flow rate of nebulizing gas: 1.04 l/min (theoretical set value)
Flow rate of curtain gas: 0.95 l/min
Corona discharge current: 0.1 µA
Voltage of heater: 12/24 V (corresponds to temperature of horizontal model, approximately 70° C./195° C.)
Other values are default values of measuring programme A clear signal was obtained when only methanol was used. Subsequently, pyridine was tested using a concentration of 10 µg/ml, and a weak signal was obtained. A better signal was obtained with 1 mg/ml of midazolam. When nitrogen was chosen as the nebulizing gas, the background disturbance signals were significantly decreased.

However, the nebulizing gas and the curtain gas flows did not have any significant effect. Only very low (nebula: 0.03-0.41 l/min, curtain: 0-0.44 l/min) and high (nebula: 1.49-1.58 l/min, curtain: 1.58-1.84 l/min) values had an effect. At low curtain gas flows, the background noise increased and with high flows the sample intensity decreased. The effect of the nebulizing gas flow varied according to the sample flow rate. At high sample flow rates (10-100 µl/min), reduction of the nebulizing gas did not have any significant effect on the peak intensity. At low flow rates (<10 µl/min) the intensity improved with growing nebulizing gas flow.

The temperature is chosen so that the examined material is vaporized well enough without the compound being degraded too much.

To improve the operation of the device, the silicon substrate can be electrically isolated from the electrode needle. This can be done for instance by building up an insulating layer of oxide or nitride, using PECVD, on the top of the metal pattern on the glass wafer. It is also possible to pattern a planar needle on the glass wafer after the bonding of the wafer. The chip can be totally made of insulating material, too.

Regarding the simplicity of the manufacturing process, a significant advantage can be achieved with planarity of the micro needle; a three-dimensional needle is more difficult to fabricate. FIG. 4 shows two modified chip configurations (glass 31 and 41, silicon 32 and 42) with a planar needle (33 and 43). The parts of the device are the same as in FIG. 3a. As FIG. 4 shows, the needle can be situated directly in front of the exit hole of the vaporisation products, parallel to the capillary, or it can be directed diagonally from the side to the front of the exit hole. A three-dimensional micro needle, 53 (see FIG. 5, device parts otherwise the same as in FIG. 3a), built on the glass and silicon wafer, 51 and 52 respectively, could be fabricated using for instance needles which are flexible due to membrane stresses, structures which are based on metal-coated polymers, needles based on bonded metal wires or micromechanically upliftable solutions, or electrochemically sharpened metal wire, for instance platinum wire.

FIGS. 6a, 6b and 7 show an alternative solution in which the nebulizing gas, which is usually inactive (or inert), such as nitrogen, comes from the top of the chip (101) through a feeding nozzle such as nanogate (102). Consequently, the gas is fed at least substantially perpendicular to the sample and not in the sample direction, as in the embodiment described above.

The thin tube marked with reference number (109) in FIGS. 6a, 6b and 7 is the connecting capillary tube coming from the liquid chromatograph (LC).

The inlets (103) for liquid and (104) for gas, respectively, have been processed in the silicon or glass wafer (101) which is on the glass plate (114). To get the capillary end positioned, wedge-shaped guides (113), which form a tapering hole, have been processed in the wafer. The wafer has been equipped with a mixing zone (105), too, to which the feeding holes (103 and 104) for liquid and gas, respectively, have been connected through the flow channels (106 and 107) (cf. also the arrows).

As the figure shows, the gas coming from the gas inlet (104) circulates, as shown by the arrows, around the end the capillary tube before it is mixed with the liquid flow in the mixing zone (105).

The wafer is equipped with heating resistors (108), which can be used to heat the liquid flow which is fed through the capillary and in which the nebulizing gas flow is mixed in the mixing zone (105), in order to vaporize the liquid. The heating resistor connectors are numbered (110) and as the figure shows the foreparts of the heating resistors are made wider in order to decrease the flow resistance, and they are made narrow only near the mixing zone of gas and liquid, where they form the actual heating zone (111) and act as heating resistors.

The solution according to FIGS. 6a, 6b and 7 is based on the same basic principle as the devices described above, but the structure according to that solution is simpler and the dead volumes are minimized. The feed nozzle of the gas is located in the direction of the liquid flow, upstream, which means that the gas is brought into the device (in the direction of the liquid flow) before the inlet opening of the liquid. Because the nebulizing gas is brought in from only one nozzle and one opening, from which it is distributed to both sides/around of the sample flow, it is easy to use this solution to generate a homogeneous mixture.

The invention claimed is:

1. A method of examining a sample by means of mass spectrometry, comprising the steps of:
   vaporizing in a vaporizer, the solution comprising the sample to be examined;
   spraying the vaporized solution using a gas flow, into a corona discharge zone, ionizing the sample to be examined, using a corona discharge, to generate gas phase ions;
   separating the gas phase ions and directing them to a detector, wherein
   the vaporiser is fabricated as a micromechanical structure;
   wherein the vaporiser includes flow channel networks for the solution and for a carrier gas for the feeding of the solution, as well as a heater, all of which are included in a monolithic structure, and
   wherein the vaporiser includes a vaporising zone and a corona discharge zone, both of which are integrated into a single micromechanical structure.

2. A method according to claim 1, wherein the flow channel networks are dimensioned so that the volume of the liquid flow passing through them is less than 100 µl/min.

3. A method according to claim 1, wherein the micromechanical structure includes flow channel networks designed for one or more wafers, and a heater.

4. A method according to claim 3, wherein the method is carried out by a structure which comprises:
   a substrate wafer in which flow channel networks for gases and liquids are formed, and
   a cover wafer, attached to the substrate wafer in which a heater for vaporising the sample solution, is patterned.

5. A method according to claim 1, further comprising ionizing, with a corona discharge in the presence of air, at a normal atmospheric pressure, the vaporized sample solution.

6. A method according to claim 1, wherein the corona discharge zone includes a needle-shaped electrode, which is connected to a voltage which is so high in relation to a curtain plate of the mass spectrometer that the electric field strength, at least in the immediate vicinity of the tip, exceeds the corona discharge threshold of air.

7. A method according to claim 6, wherein the potential of the needle-shaped electrode in relation to a curtain plate is at least 1 kV, and the maximum electric field strength near the tip of the electrode is approximately 50 kV/mm.

8. A method according to claim 1, further comprising the step of examining polar compounds, non-polar compounds, neutral compounds or ionic compounds, and the sample to be examined is dissolved in a polar or non-polar solvent, used as the eluent, to generate the sample solution.

9. A method according to claim 8, further comprising the step of examining the compounds, the molar masses of which are at most 2000 Da.

10. The method according to claim 8, further comprising the step of examining the compounds, the molar masses of which are at most 1000 Da.

11. A method according to claim 1, further comprising the step of feeding the flow of liquid of the sample to be examined at a value which is lower than approximately 10 µl/min, and the flow of a carrier gas used for feeding the sample is set at a value which is at least approximately 50 µl/min.

12. A method according to claim 1, further comprising the step of ionizing the sample using the Atmospheric Pressure Chemical Ionization (APCI) method.

13. A method according to claim 1, further comprising the step of bringing in essentially perpendicular to the flow direction of the sample the gas flow used for the injection.

14. A method according to claim 13, further comprising the step of feeding the gas flow through a feed opening, in order to distribute the gas flow around the liquid flow comprising the vaporized sample solution, and, as a result, a homogeneous mixture is achieved.

15. A method according to claim 1, further comprising the step of feeding the gas flow into the device in the flow direction of the vaporized sample solution, before and around a feed opening of the vaporized sample solution.

16. A method according to claim 1, wherein the flow channel networks are dimensioned so that the volume of the liquid flow passing through them is less than 10 µl/min.

17. An apparatus for examining a sample by means of mass spectrometry, comprising
a vaporiser for vaporising a solution comprising the sample to be examined,
a corona discharge device, connected to the vaporiser, in which the sample to be examined is ionised according to the Atmospheric Pressure Chemical Ionization (APCI) method, to generate charged particles,
a detector, connected to the corona discharge device, to detect charged particles,
means for directing the charged particles, using electric and magnetic fields, from the corona discharge device to a detector, and
the vaporiser is fabricated as a micromechanical structure;
wherein the vaporiser includes flow channel networks for the solution and for a carrier gas for the feeding of the solution, as well as a heater, all of which are included in a monolithic structure, and
wherein the vaporiser includes a vaporising zone and a corona discharge zone, both of which are integrated into a single micromechanical structure.

18. An apparatus according to claim 17, wherein the flow channel networks are dimensioned so that the volume of the liquid flow passing through them is less than 100 µl/min.

19. An apparatus according to claim 17, further comprising:
said micromechanical structure includes a monolithic block which is formed of two or more parts which are connected to each other.

20. An apparatus according to claim 19, further comprising:
the monolithic block comprises a silicon wafer in which flow channel networks for gases and liquid sample are formed, and a glass plate in which a heater for vaporising the sample solution is formed.

21. An apparatus according to claim 19, further comprising:
the monolithic block includes a glass plate in which flow channel networks for gases and liquid are formed, and a silicon wafer in which a heater for vaporising the sample solution is formed.

22. An apparatus according to claim 17, further comprising:
the corona discharge device includes a needle-shaped electrode, which is connected to a potential which is so high in relation to a curtain plate of the mass spectrometer that the electric field strength, at least in the immediate vicinity of the tip of the electrode, exceeds the corona discharge threshold of air.

23. An apparatus according to claim 22, wherein the potential of the needle-shaped electrode in relation to a curtain plate is set at a value which is at least 1 kV, and the maximum strength of the electric field near the tip of the electrode is set at least at approximately 50 kV/mm.

24. An apparatus according to claim 17, further comprising:
the micromechanical structure is fabricated entirely as a glass structure.

25. An apparatus according to claim 17, further comprising:
the flow channel system of the carrier gas used for feeding the solution is connected to a feed nozzle of the gas, which nozzle is located upstream in the flow direction of the vaporized sample solution and through which gas can be fed into the device essentially perpendicular to the flow direction of the sample solution.

26. A device according to claim 25, further comprising:
the gas flow fed through the feed nozzle is distributed before and around a vaporized solution feed nozzle of the flow channel networks in order to achieve a homogeneous mixture.

27. A device according to claim 17, further comprising:
the heater includes heating resistors, the foreparts of which are made wide in order to decrease the flow resistance and which are made narrow only near the mixing zone of gas and liquid, where they act as heating resistors and form the actual heating zone.

28. The apparatus of claim 17, further comprising:
said flow channel system includes wedge-shaped guides which form a tapering hole at a discharge end.

29. An apparatus according to claim 17, wherein the flow channel networks are dimensioned so that the volume of the liquid flow passing through them is less than 10 µl/min.

30. An apparatus for examining a sample by means of mass spectrometry, comprising
a vaporiser for vaporising a solution comprising the sample to be examined, a corona discharge device, connected to the vaporiser, in which the sample to be examined is ionised according to the Atmospheric Pressure Chemical Ionization (APCI) method, to generate charged particles, a detector, connected to the corona discharge device, to detect charged particles, means for directing the charged particles, using electric or magnetic fields, from the corona discharge device to a detector, and the vaporiser is fabricated as a micromechanical structure;

wherein the vaporiser includes flow channel networks for the solution and for a carrier gas for the feeding of the solution, as well as a heater, all of which are included in a monolithic structure, and wherein the vaporiser includes a vaporising zone and a corona discharge zone, both of which are integrated into a single micromechanical structure.

* * * * *